United States Patent
Ku et al.

(10) Patent No.: US 7,271,719 B2
(45) Date of Patent: Sep. 18, 2007

(54) RFID SYSTEM FOR MONITORING FOOD HYGIENE

(75) Inventors: Chun-Hui Ku, Taipei (TW); Wei Chang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 197 days.

(21) Appl. No.: 11/115,156

(22) Filed: Apr. 27, 2005

(65) Prior Publication Data

US 2006/0214788 A1 Sep. 28, 2006

(30) Foreign Application Priority Data

Mar. 15, 2005 (TW) .............................. 94107808 A (51) Int. Cl.
*G08B 1/08* (2006.01)
(52) U.S. Cl. .......................... 340/539.26; 340/539.16; 340/572.1; 340/10.1
(58) Field of Classification Search .......... 340/539.16, 340/539.13, 539.22, 539.26, 505, 572.1, 340/572.7, 572.8, 521, 10.1, 531

See application file for complete search history.

(56) References Cited

U.S. PATENT DOCUMENTS

| | | | |
|---|---|---|---|
| 6,294,997 B1 | 9/2001 | Paratore et al. | 340/572.1 |
| 6,982,640 B2* | 1/2006 | Lindsay et al. | 340/540 |
| 7,009,517 B2* | 3/2006 | Wood | 340/572.1 |
| 7,019,640 B2* | 3/2006 | Canich et al. | 340/531 |
| 7,148,803 B2* | 12/2006 | Bandy et al. | 340/539.16 |
| 2004/0041714 A1 | 3/2004 | Forster | 340/870.17 |
| 2004/0100380 A1 | 5/2004 | Lindsay et al. | 340/540 |

FOREIGN PATENT DOCUMENTS

CN 490640 11/1988

* cited by examiner

*Primary Examiner*—Anh V. La
(74) *Attorney, Agent, or Firm*—Troxell Law Office, PLLC (57) ABSTRACT

The present invention discloses a RFID system for monitoring food hygiene, comprising: a first accommodating space; an object-under-monitor with a RFID tag attached thereon, being disposed in the first accommodating space; an environmental sensor, disposed in the first accommodating space; a processor, electrically connected to the environmental sensor; a first RFID accessing device, disposed in the first accommodating space while electrically connected to the processor; a second accommodating space; a displaying device, disposed in the second accommodating space; and a second RFID accessing device, disposed in the second accommodating space while electrically connected to the displaying device.

16 Claims, 5 Drawing Sheets

RFID SYSTEM FOR MONITORING FOOD HYGIENE

FIELD OF THE INVENTION

The present invention relates to a food hygiene control system, and more particularly, to a radio frequency identification (RFID) system for monitoring and controlling food hygiene.

BACKGROUND OF THE INVENTION

The demand for frozen foods is driven by the ever changing consumers and their lifestyle. Consumers are spending less time per day preparing meals at home, and their time-starved, fast-paced lifestyles have them searching for alternative meal solutions. Changes in demographics have also created a need for good tasting, affordable, healthy, yet convenient food. However, frozen foods pass through numerous handlers during the distribution process (the "cold chain"). If a frozen food product is not properly handled throughout each link in the cold chain, i.e. it is exposed to an environmental condition of improper temperature, the thawing of the perishable frozen food will cause the quality and taste of the frozen food to deteriorate.

It is doubtful and difficult to prove that the frozen food products are kept in a proper temperature range during the cold chain. The failing of providing substantial data of temperature control during shipment by the frozen food distributors helps to create reasonable doubt about the hygiene of frozen food, especially when there is disadvantageous news about the quality of food product. Without the data of temperature control, it is difficult to specify exactly which part of the cold chain is the one to blame while the quality problem of the shipped frozen food occurs.

Figure 1:
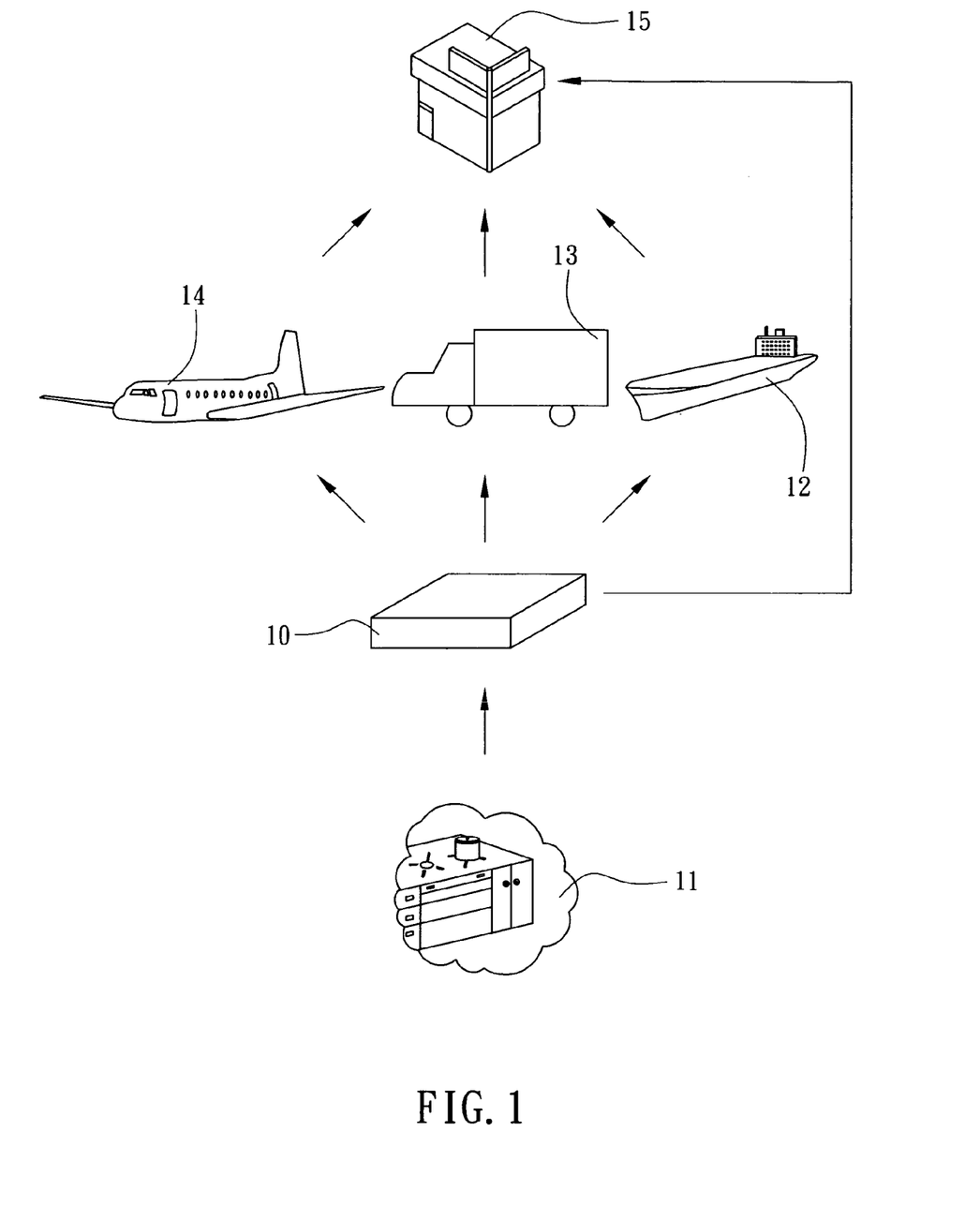
FIG. 1 is a schematic diagram depicting a distribution process of food product.

As seen in FIG. 1, as a food product 10 leaves a kitchen 15, it may be shipped by a transportation means like a ship 12, a truck 14, or an airplane 15, to be distributed to a retailer 15. The quality problem of the shipped frozen food might occur during the distribution if the temperature control of any one of the links in the cold chain of FIG. 1 is failed. Thus, how to control the hygiene of frozen food during the shipment in the cold chain becomes an urgent problem that has to be overcome.

Recently, as the advance of RFID technology, there are some patented RFID devices that can be used in the field of food hygiene control, such as the RFID devices disclosed in R.O.C. Pat. No. 460640, entitled "Method, Electronic Tag and System for Reporting Dynamic Properties of a Product Using Radio Frequency Identification Device Technology", in U.S. Pat. No. 6,294,997, entitled "RFID Tag Having Timing and Environment Modules", in U.S. Published Application No. 2004/0100380, entitled "RFID System and Method for Tracking Food Freshness", and in U.S. Published Application No. 2004/0041714, entitled "RFID temperature device and method".

In the R.O.C. Pat. No. 460640, an electronic tag equipped with a sensor is provided, which can determine dynamic properties of a product when the tag is activated, The dynamic properties of the product are then either further processed into other dynamic properties. In any even either the former or the latter dynamic properties are then transmitted from the tag. Such dynamic properties could be the temperature of a product or the expiration data of the product derived from periodic measurements of the temperature of the product.

In U.S. Pat. No. 6,294,997, an RFID tag is provided with a timing module to measure elapsed time and an environment module to detect certain environmental conditions. The RFID tag includes a transmitter/receiver, memory module, antenna module, converter, and the timing and environment modules. In an embodiment of the invention, the timing module enables the user, upon interrogating the RFID tag, to determine the precise length of time from the previous charge of the RFID tag. The environment module enables the user to determine how long the RFID tag has been exposed to certain environmental conditions that have been pre-defined by the user.

In U.S. Published Application No. 2004/0100380, a method is provided for tracking the freshness or expiration dates of food products put into storage. The food products placed into storage are provided with smart tags, the smart tags containing food product information regarding the freshness or expiration date of the food product. The food products are scanned with a smart tag scanner prior to placing the products into storage, the scanner configured to retrieve the food product information from the smart tags. The user may be alerted if the retrieved information indicates that the food product being placed into storage has expired or is no longer fresh. The food products are placed in storage, and the user may be alerted when any of stored products have expired or are no longer fresh.

In U.S. Published Application No. 2004/0041714, a remote communication device is provided that receives temperature indicia concerning a container and/or its contents and communicates such temperature indicia along with an identification indicia to a reader. The remote communication device can measure and communicate temperature indicia associated with a container in a periodic manner. The remote communication device can also measure and communicate temperature indicia associated with a container when such temperature indicia exceed a certain minimum or maximum threshold temperature. The remote communication device can also include power circuitry to store energy when energized in the range of an interrogation reader so that the remote communication device can be powered for temperature indicia measurements when not in the range of an interrogation reader.

The operating principle of the abovementioned prior-art RFID devices is that the RFID tag equipped with batteries and sensors is configured to record the length of time from the previous charge of the RFID tag and how long the RFID tag has been exposed to certain environmental conditions. The kind of the abovementioned prior-art RFID devices relay on the batteries arranged therein for providing power to the environment module to detect certain environmental conditions. Once the power reserved in the battery is low that is not detected in time, the normal recording and detecting of the environment module can be adversely affect that even cause previously recorded environmental data to loss. In addition, the cost of the abovementioned active RFID devices is high that the popularization of the active RFID devices might not be feasible. Besides, the abovementioned prior-art RFID devices still unable to provide substantial data of temperature control during shipment to be access easily by consumers that the reasonable doubt about the hygiene of frozen food still can not be avoided.

Therefore, it is required to have a RFID system capable of monitoring food hygiene during the shipment.

SUMMARY OF THE INVENTION

It is the primary object of the invention to provide a RFID system for monitoring food hygiene, which is capable of tracking the freshness of food products by using a RFID tag to detect and record certain environmental conditions, e.g. temperature and moisture, during a distribution process.

It is the another object of the invention to provide a RFID system for monitoring food hygiene, capable of providing a series of environmental data recorded during a distribution process so as to specify exactly which part of the distribution process is the one to blame while the quality problem of the shipped food occurs.

To achieve the above object, the present invention provides a RFID system for monitoring food hygiene, comprising:

a first accommodating space;
an object-under-monitor, having a RFID tag attached thereon and being disposed in the first accommodating space;
an environmental sensor, disposed in the first accommodating space;
a processor, electrically connected to the environmental sensor;
a first RFID accessing device, disposed in the first accommodating space while electrically connected to the processor;
a second accommodating space;
a displaying device, disposed in the second accommodating space; and
a second RFID accessing device, disposed in the second accommodating space while electrically connected to the displaying device.

To achieve the above object, the present invention provides a RFID food hygiene control method, comprising the steps of:

(a) providing a first accommodating space, an object-under-monitor with a RFID tag attached thereon being disposed in the first accommodating space, an environmental sensor disposed in the first accommodating space, a processor electrically connected to the environmental sensor, a first RFID accessing device disposed in the first accommodating space while electrically connected to the processor, a second accommodating space, a displaying device disposed in the second accommodating space, and a second RFID accessing device disposed in the second accommodating space while electrically connected to the displaying device;

(b) enabling the environmental sensor to detect specific information of the first accommodating space;

(c) transmitting the detected information from the environmental sensor to the processor;

(d) using the first RFID accessing device enabled by the processor to write the detected information into the RFID tag;

(e) moving the object-under-monitor from the first accommodating space to the second accommodating space;

(f) using the second RFID accessing device to read the information resided in the RFID tag;

(g) displaying the information by the displaying device.

In a preferred embodiment of the invention, the RFID system for monitoring food hygiene further comprises an alarm device, which is electrically connected to the second RFID accessing device, and thus, preferably, the RFID food hygiene control method further comprise the steps of:

(f1) providing an alarm device, being electrically connected to the second RFID accessing device;

(f2) enabling the alarm device to issue an alerting signal.

Preferably, the object-under-monitor is a food product.

Preferably, the connection between the first RFID accessing device and the processor is achieved by a means selected from the group consisting of a wired connection and a wireless connection.

Preferably, the RFID tag is a passive RFID tag.

Preferably, the specific information detected by the environmental sensor include at least one subject selected from the group consisting of temperature and moisture.

Preferably, the RFID food hygiene control method further comprise the step of: (d1) using the first RFID accessing device enabled by the processor to write the positioning of the first accommodating space and the exact time of the RFID tag being interrogated by the first RFID accessing device after the detected information being written into the RFID tag.

Preferably, the RFID tag is equipped with a clipping holder for the RFID tag to attach thereto, which used for accommodating the object-under-monitor.

In a preferred embodiment of the invention, the RFID food hygiene control method further comprises the steps of:

(h) detaching the clipping holder from the object-under-monitor;

(i) deleting the information resided in the RFID tag.

Other aspects and advantages of the present invention will become apparent from the following detailed description, taken in conjunction with the accompanying drawings, illustrating by way of example the principles of the present invention.

BRIEF DESCRIPTION OF THE DRAWINGS

FIG. 3, which is composed of FIG. 3A, FIG. 3B and FIG. 3C, is a flowchart of the RFID food hygiene control method according to the present invention.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as the follows.

Figure 2:
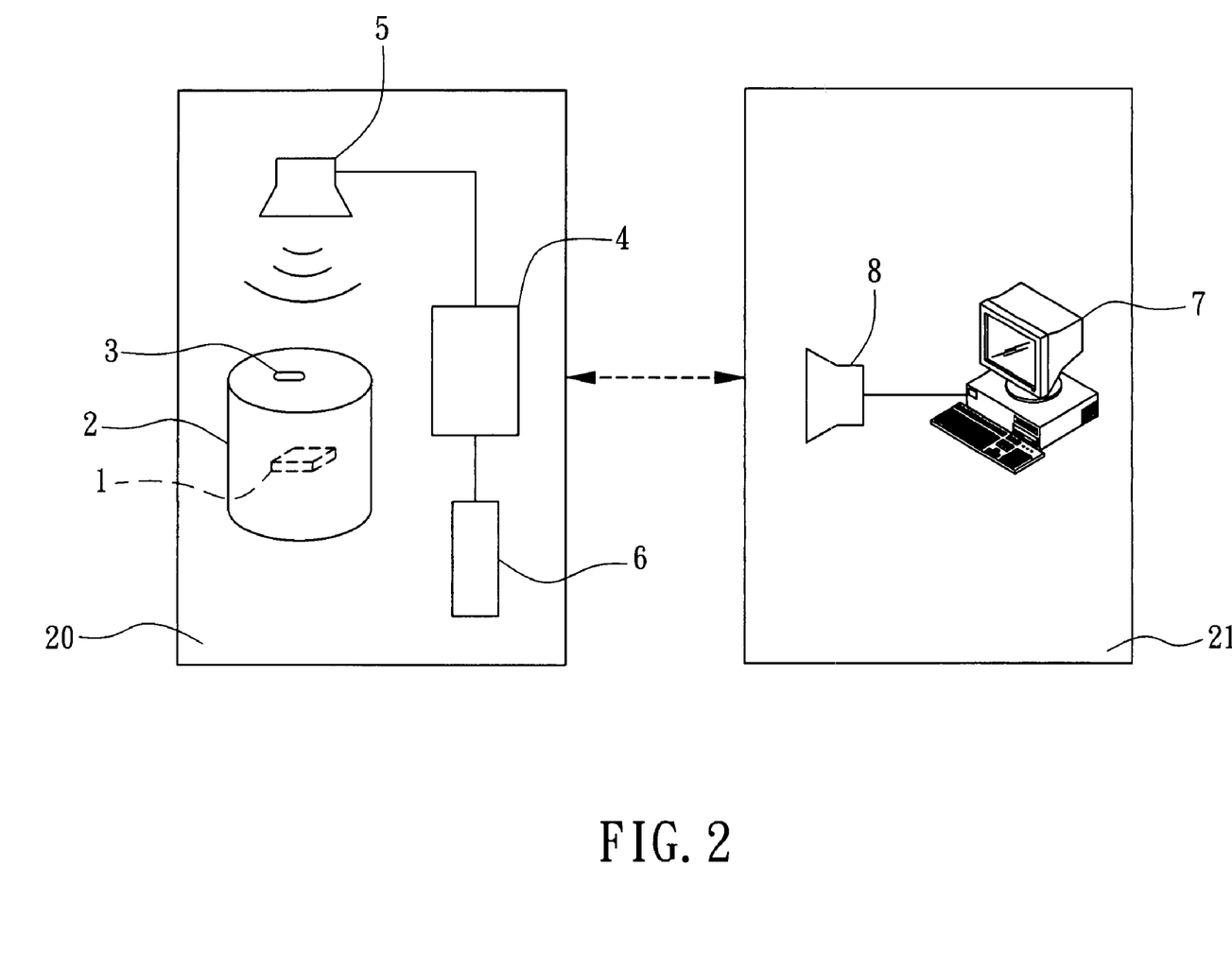
FIG. 2 is a schematic view of the RFID system for monitoring food hygiene according to the present invention.

Please refer to FIG. 2, which is a schematic view of the RFID system for monitoring food hygiene according to the present invention. As seen in FIG. 2, the RFID system comprises: a storing space 20, which can be a container; a billing space 21, having a displaying device 7 and a RFID reader 8 disposed therein; a holder 2 with a RFID tag 3 attached thereto; a food product 1, disposed inside the holder 2; an environmental sensor 6, capable of detecting environmental information like temperature and moisture and transmitting the detected information to a micro processor 4; the micro processor 4, for processing the detected information transmitted from the sensor 6; and a RFID reader 5, being activated by the micro processor 4 to write the detected information into the RFID tag 3 along with the time of detection; wherein the micro processor 4, the RFID reader 5 and the environmental sensor 6 are disposed in a storing space 20 while electrically connected to each other, and the displaying device 7 is electrically connected to the RFID reader 8.

As the holder 2 with the food product 1 disposed therein is transported to the billing space 21, such as a convenient store, and is purchased by a consumer, the RFID tag 3 attached to the holder 2 will be read by the RFID reader 8 so that the information relating to a distribution process of the food product 1 like temperature and expiration date is displayed on the displaying device 7 enabling the consumer to confirm the freshness of the food product 1. Thereafter, the food product 1 is removed from the holder 2 so that the holder 2 along with the RFID tag 3 attached thereto can be recycled.

Figures 3, 3A:
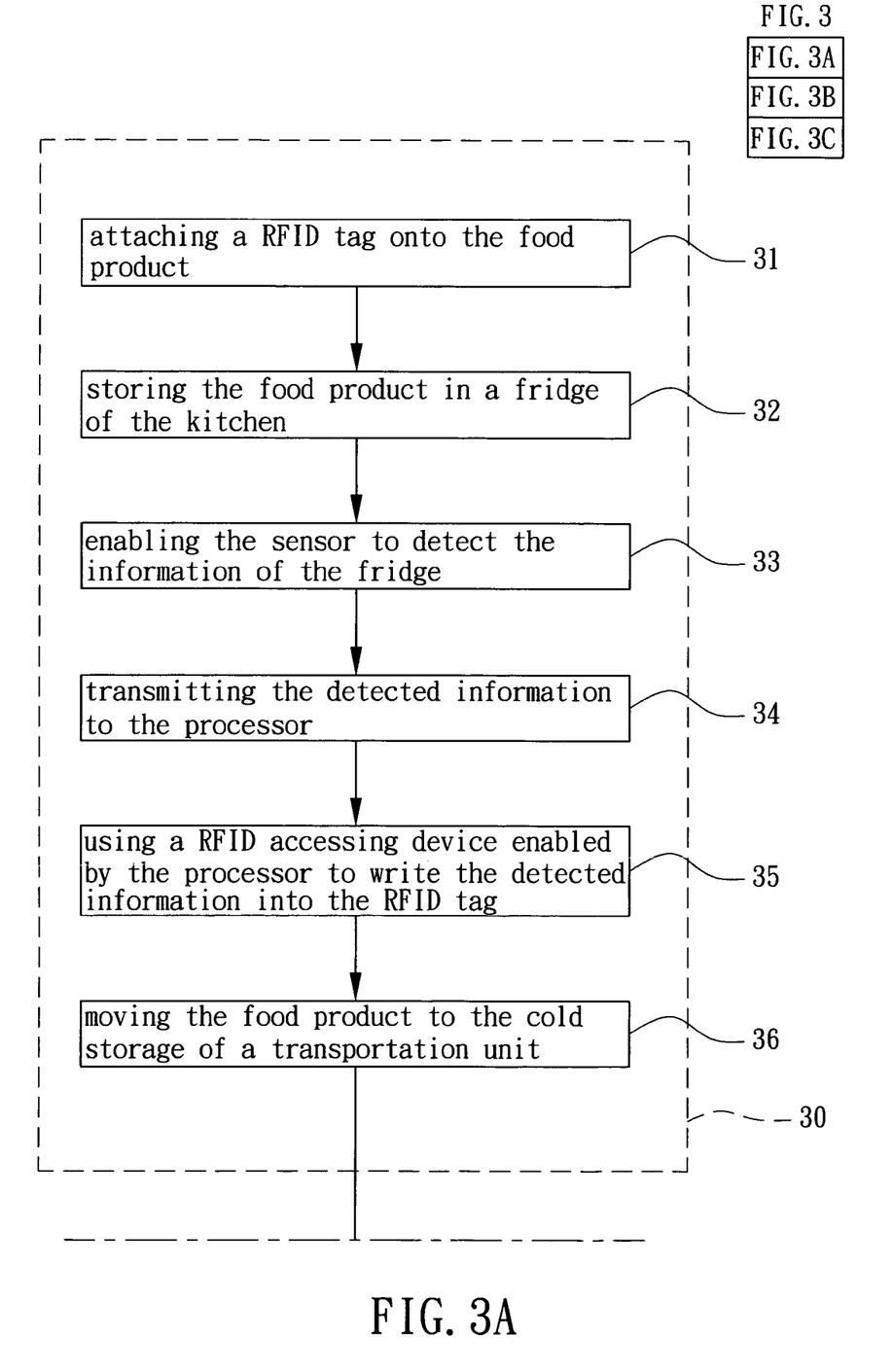
Figure 3B:
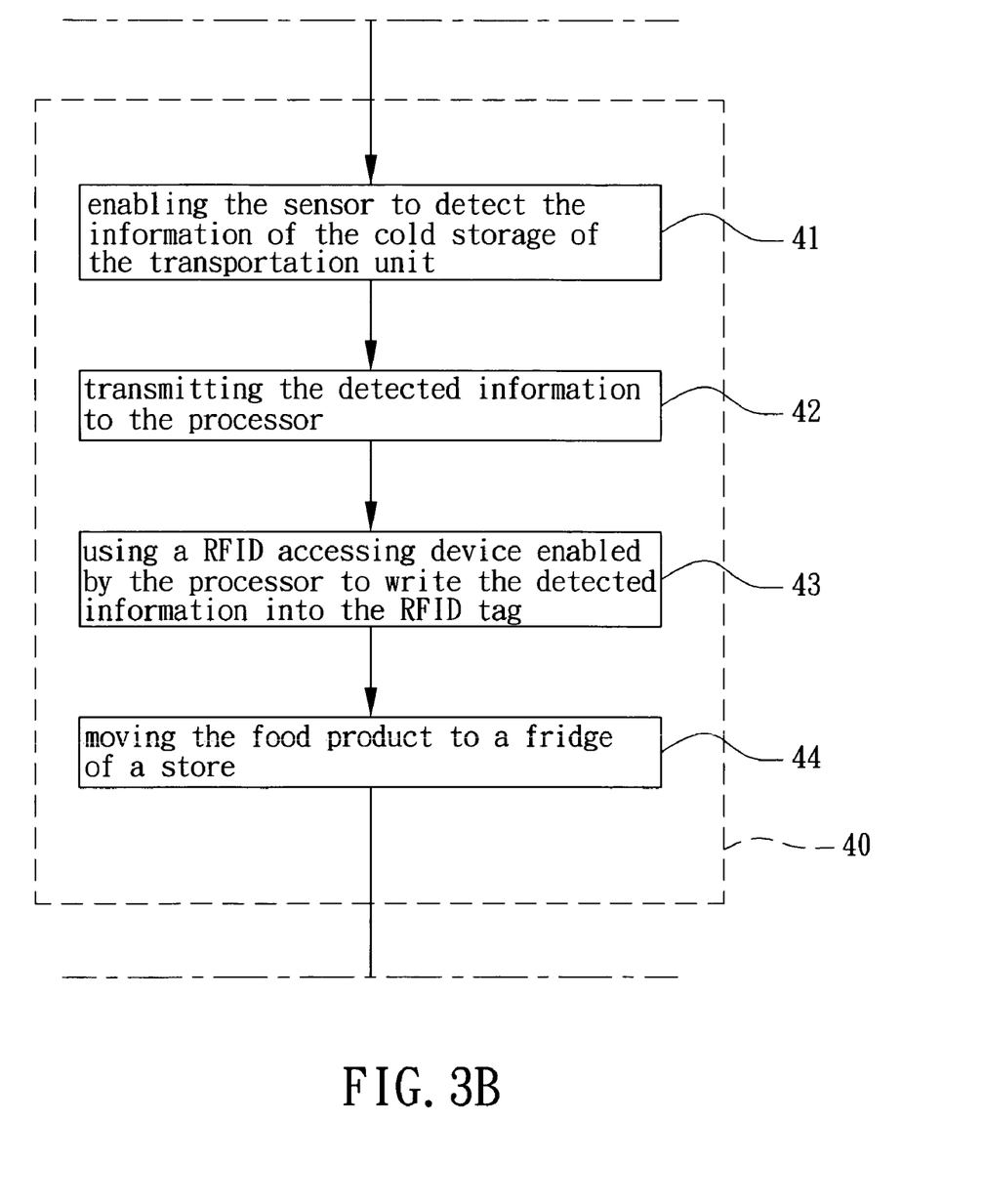
Figure 3C:
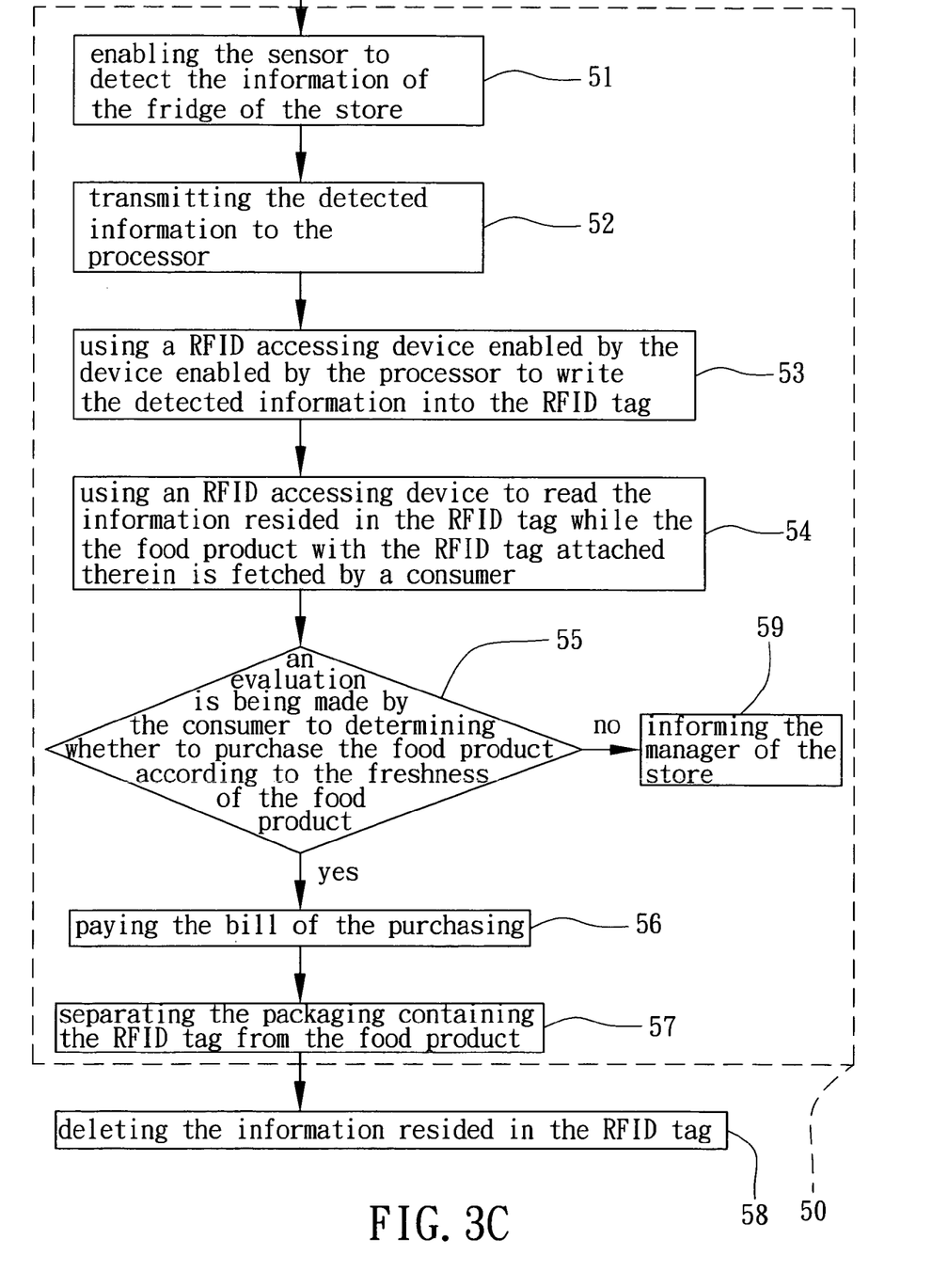

Please refer to FIG. 3, which is composed of a production stage 30 shown in FIG. 3A, a distribution stage 40 shown in FIG. 3B and a sale stage 50 shown in FIG. 3C and is a flowchart of the RFID food hygiene control method according to the present invention.

FIG. 3A is a flow chart of production stage 30 showing the process of a food product after being produced by a kitchen. The production stage of FIG. 3A comprises the steps of:

step 31: attaching a RFID tag onto the food product; in that the attaching can be performed as putting the food product inside a container with passive RFID tag 3 attached thereto while encoding the basic information of the food product 1 into the RFID tag, wherein the container has a distinct identification code, and the basic information includes manufacture date, expiration date, ingredients, and so on;

step 32: storing the food product in a fridge of the kitchen;

step 33: enabling the sensor to detect the information of the fridge, wherein the information includes the temperature and moisture of the fridge;

step 34: transmitting the detected information to the processor, wherein the transmitting can be performed in a manner of wired transmission or wireless transmission;

step 35: using a RFID accessing device enabled by the processor to write the detected information into the RFID tag, wherein the connection between the first RFID accessing device and the processor is achieved by a means selected from the group consisting of a wired connection and a wireless connection;

step 36: moving the food product to the cold storage of a transportation unit, wherein the transportation unit can be a ship, a truck or an airplane, etc.

FIG. 3B is a flow chart of distribution stage 40. The distribution stage of FIG. 3B comprises the steps of:

step 41: enabling the sensor to detect the information of the cold storage of the transportation unit, wherein the information includes the temperature and moisture of cold storage of the transportation unit;

step 42: transmitting the detected information to the processor, wherein the transmitting can be performed in a manner of wired transmission or wireless transmission;

step 43: using a RFID accessing device enabled by the processor to write the detected information into the RFID tag, wherein the connection between the first RFID accessing device and the processor is achieved by a means selected from the group consisting of a wired connection and a wireless connection;

step 44: moving the food product to a fridge of a store.

FIG. 3C is a flow chart of sale stage 40. The sale stage of FIG. 3C comprises the steps of:

step 51: enabling the sensor to detect the information of the fridge of the store, wherein information includes the temperature and moisture of the fridge of the store;

step 52: transmitting the detected information to the processor, wherein the transmitting can be performed in a manner of wired transmission or wireless transmission;

step 53: using a RFID accessing device enabled by the processor to write the detected information into the RFID tag, wherein the connection between the first RFID accessing device and the processor is achieved by a means selected from the group consisting of a wired connection and a wireless connection, and as the detected information indicates a specific limit being exceeded, i.e. the food product is not fresh, the manager of the store is informed so that the manager can remove the stale food product using a handheld RFID reader;

step 54: using an RFID accessing device to read the information resided in the RFID tag while the food product with the RFID tag attached thereto is fetched by a consumer, wherein the RFID accessing device is disposed outside the fridge of the store or at the billing counter of the store;

step 55: an evaluation is being made by the consumer to determining whether to purchase the food product according to the freshness of the food product as the detected information is displayed on the displaying device to be review by the consumer;

step 56: paying the bill of the purchasing while the consumer decide to purchase the food product;

step 57: separating the container containing the RFID tag from the food product so as to recycle the container along with the RFID tag;

step 58: deleting the information resided in the RFID tag, where the deleting can be perform in a recycle factory;

step 59: informing the manager of the store while the consumer decide not to purchase the food product since the information revealed on the displaying device indicates that the food product is not fresh, and thereafter the manager of the store is informed so that the manager can remove the stale food product using a handheld RFID reader.

In a preferred embodiment of the invention, the RFID tag can be a passive RFID tag, and the connection between the first RFID accessing device and the processor is achieved by a means selected from the group consisting of a wired connection and a wireless connection, moreover, the interrogation time as well as the positioning and coding of the accommodating space, such as the fridge of the kitchen, the cold storage of the truck and the fridge of the store, are written into the RFID tag by the processor simultaneously while the processor is writing the detected information like temperature and moisture into the RFID tag.

In another preferred embodiment, the RFID tag is integrally formed with the environmental sensor such that the RFID tag is capable of detecting the environmental conditions like temperature and moisture by itself and thus enables the RFID system of the present invention to have a simpler structure.

Furthermore, the RFID system of the present invention further comprises an alarm device, which can be set up at the billing counter of a store or just outside the fridge of the store and is electrically connected to the RFID accessing device. The alarm device can be triggered to issue an alerting signal like a beeping sound or a flash to while the RFID accessing device detect a certain information resided in the RFID tag of a food product exceeds a specific standard value as the RFID accessing device is writing data therein or is reading data therein, by that a customer or a manager of the store can be remind that the corresponding food product is not in a desirable condition.

From the above description, it is noted that the RFID system of the present invention is capable of informing food hygiene condition to a consumer in real-time, monitoring food hygiene condition during the whole distribution process without external support, and reducing manufacturing cost by recycling the RFID tag.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A RFID system for monitoring food hygiene, comprising:
   a first accommodating space;
   an object-under-monitor with a RFID tag attached thereon, being disposed in the first accommodating space, the RFID tag is recycled by selectively deleting information stored therein;
   an environmental sensor, disposed in the first accommodating space;
   a processor, electrically connected to the environmental sensor;
   a first RFID accessing device, disposed in the first accommodating space while electrically connected to the processor;
   a second accommodating space;
   a displaying device, disposed in the second accommodating space; and
   a second RFID accessing device, disposed in the second accommodating space while electrically connected to the displaying device,
   wherein the environmental sensor is integrally formed with the RFID tag.

2. The RFID system of claim 1, wherein the object-under-monitor is a food product.

3. The RFID system of claim 1, wherein the connection between the first RFID accessing device and the processor is achieved by a means selected from the group consisting of a wired connection and a wireless connection.

4. The RFID system of claim 1, wherein the RFID tag is a passive RFID tag.

5. The RFID system of claim 1, wherein information detected by the environmental sensor include at least one subject selected from the group consisting of temperature and moisture.

6. The RFID system of claim 1, further comprises a clipping holder for the RFID tag to attach thereto, being used for accommodating the object-under-monitor.

7. The RFID system of claim 1, further comprises an alarm device, electrically connected to the second RFID accessing device.

8. RFID food hygiene control method, comprising the steps of:
   (a) providing a first accommodating space, an object-under-monitor with a RFID tag attached thereon being disposed in the first accommodating space, an environmental sensor disposed in the first accommodating space, a processor electrically connected to the environmental sensor, a first RFID accessing device disposed in the first accommodating space while electrically connected to the processor, a second accommodating space, a displaying device disposed in the second accommodating space, and a second RFID accessing device disposed in the second accommodating space while electrically connected to the displaying device, the environmental sensor is integrally formed with the RFID tag;
   (b) enabling the environmental sensor to detect specific information of the first accommodating space;
   (c) transmitting the detected information from the environmental sensor to the processor;
   (d) using the first RFID accessing device enabled by the processor to write the detected information into the RFID tag;
   (e) moving the object-under-monitor from the first accommodating space to the second accommodating space;
   (f) using the second RFID accessing device to read the information resided in the RFID tag;
   (g) displaying the information by the displaying device, and
   (h) deleting the information stored in the RFID tag.

9. The method of claim 8, wherein the object-under-monitor is a food product.

10. The method of claim 8, wherein the connection between the first RFID accessing device and the processor is achieved by a means selected from the group consisting of a wired connection and a wireless connection.

11. The method of claim 8, wherein the RFID tag is a passive RFID tag.

12. The method of claim 8, wherein the specific information detected by the environmental sensor includes at least one subject selected from the group consisting of temperature and moisture.

13. The method of claim 8, further comprising the step of:
   (d1) using the first RFID accessing device enabled by the processor to write the positioning of the first accommodating space and the exact time of the RFID tag being interrogated by the first RFID accessing device after the detected information being written into the RFID tag.

14. The method of claim 8, wherein a clipping holder is further provided for the RFID tag to attach thereto, being used for accommodating the object-under-monitor.

15. The method of claim 14, further comprising the step of:
   (i) detaching the clipping holder from the object-under-monitor.

16. The method of claim 8, further comprising the steps of:
   (f1) providing an alarm device, being electrically connected to the second RFID accessing device;
   (f2) enabling the alarm device to issue an alerting signal.

* * * * *

UNITED STATES PATENT AND TRADEMARK OFFICE
CERTIFICATE OF CORRECTION

PATENT NO. : 7,271,719 B2  
APPLICATION NO. : 11/115156  
DATED : September 18, 2007  
INVENTOR(S) : Chun-Hui Ku et al.

It is certified that error appears in the above-identified patent and that said Letters Patent is hereby corrected as shown below:

On the title page, item (30) should read as follows:

--(30) Foreign Application Priority Data
    Mar. 25, 2005    (TW) ............................... 94109250--

Signed and Sealed this

Eighteenth Day of December, 2007

JON W. DUDAS  
*Director of the United States Patent and Trademark Office*